US012714299B2

(12) United States Patent
Pal et al.

(10) Patent No.: US 12,714,299 B2
(45) Date of Patent: Aug. 25, 2026

(54) DEVICE FOR GENERATING A TOROIDAL SOURCE OF ILLUMINATION

(71) Applicant: Forus Health Pvt. Ltd., Bangalore (IN)

(72) Inventors: Sourav Pal, Bangalore (IN); Ranjith Kumar, Bangalore (IN); Ronal Issac Vettikattu, Bangalore (IN); Justin Antony, Bangalore (IN)

(73) Assignee: Forus Health Pvt. Ltd., Bangalore (IN)

( * ) Notice: Subject to any disclaimer, the term of this patent is extended or adjusted under 35 U.S.C. 154(b) by 453 days.

(21) Appl. No.: 18/472,487

(22) Filed: Sep. 22, 2023

(65) Prior Publication Data

US 2024/0074650 A1 Mar. 7, 2024

(30) Foreign Application Priority Data

Sep. 24, 2022 (IN) ............................. 202241054830

(51) Int. Cl.
*A61B 3/00* (2006.01)
*A61B 3/10* (2006.01)

(52) U.S. Cl.
CPC ............ *A61B 3/0008* (2013.01); *A61B 3/101* (2013.01)

(58) Field of Classification Search
CPC .............................. A61B 3/0008; A61B 3/101
USPC .......................................................... 351/221
See application file for complete search history.

(56) References Cited

U.S. PATENT DOCUMENTS 8,899,753 B2 12/2014 Steinmueller
2010/0079726 A1* 4/2010 Carbonari .............. A61B 3/107 351/212
2013/0050648 A1* 2/2013 Steinmueller .......... A61B 3/101 351/246
2013/0128225 A1* 5/2013 Wall ..................... G02B 17/008 351/221

FOREIGN PATENT DOCUMENTS

CN 102961121 A 3/2013
CN 108601521 A 9/2018
DE 2544561 A1 4/1976
EP 1854152 A2 11/2007
WO 2007042854 A1 4/2007

OTHER PUBLICATIONS

First Examination Report for Indian Application No. 202241054830, dated Dec. 16, 2025.

* cited by examiner

*Primary Examiner* — Sharrief I Broome
(74) *Attorney, Agent, or Firm* — The Belles Group, P.C.

(57) ABSTRACT

Disclosed is a device for generating a toroidal source of illumination is disclosed. The device comprises a translucent disc with a concentric hole. A planar coil of side emitting optic fiber is disposed on one surface of the disc. The coil is energized with an LED at one end of the coil. The light emitted by the side of the coil is randomly scattered by the disc producing a toroidal source of light at the other surface of the disc. This source is used with instruments for assessing the dryness of the human eye. Further embodiments describe adaptations for measuring tear breakup time and the height of the tear meniscus in the human eye.

12 Claims, 7 Drawing Sheets

A

B

DEVICE FOR GENERATING A TOROIDAL SOURCE OF ILLUMINATION

CROSS-REFERENCE TO RELATED PATENT APPLICATIONS

This U.S. non-provisional patent application claims priority to Indian Patent Application No. 202241054830, filed on Sep. 24, 2022. The disclosure of the aforementioned priority application is incorporated herein by reference in its entirety.

FIELD OF THE DISCLOSURE

This disclosure belongs to the field of light sources. In particular, it belongs to the field of light sources for ophthalmic instruments.

BACKGROUND TO THE DISCLOSURE

The number of people suffering from the problem of dry eyes is increasing. This may be attributed to many factors such as increased use of handheld electronic devices, computers at home and at work requiring many hours of looking at the screens, increased TV viewing time, dry air in air-conditioned spaces, air pollution, and so on.

Thus, ophthalmologists and other eye care professionals (hereinafter referred to as a user) need to assess the severity of the problem when a subject presents with dry eyes. There are several methods of assessing dryness in the eyes and some of them are as follows.

The eye of the subject being assessed for dry eyes is illuminated by a light source having a large uniformly bright area, referred to as an extended light source. Due to this extended light source, fringes of equal inclination form over lipid layer—the outermost layer of tear film on the cornea of the subject under assessment. This is imaged and captured using an imaging system. The color and distribution of interference fringes varies with the thickness of lipid layer. Understanding of lipid layer thickness allows the user to understand the condition of dry eye noninvasively.

Thus, a toroidal extended light source (hereinafter, a toroidal light source) is used to illuminate the eye and an electronic camera with video capabilities, for example, is arranged at the central hole of the toroid and is used to capture the image of the eye illuminated by the toroidal light source. The camera may have additional optics for capturing a well-focused image. Either manual or automated analysis of the captured images and videos can lead to an assessment of the dryness of the subject's eye.

Another method of assessing a subject's eyes for dryness is to measure the height of the tear meniscus. Tear meniscus is the tear accumulated over the top edge of the lower lid of the eye, immediately after a complete blink. Greater the amount of tear in the eye, greater will be the height of the tear meniscus. Therefore, height of the tear meniscus (TMH) is a good measure of the dryness or lubrication of the eye.

To measure the height of the meniscus the image of the subject's eye must be captured from a predetermined distance so that the number of pixels in the image may be correlated with length, say in mm. To enable this, an image of a ring may be projected on to the eye of the subject from a predetermined distance. The camera is then moved such that the ring, as measured in the image, is of a predetermined size. Once this is done, the correlation between the number of pixels in the image and length may be calculated in a known way. Then, the height of the tear meniscus can be measured from the number of pixels covered by the meniscus in the image.

Such a device for measuring TMH may use a toroidal light source similar to the one described above, which additionally has a dark opaque ring on it. Thus, when the cornea of the subject is illuminated by the toroidal light source with an opaque ring in the light path, the image of the ring is formed on the cornea of the subject which may be captured by the camera as described above and the height of the meniscus measured.

It is well-known that the layer of tear formed on the surface of the eye is periodically refreshed by blinking. It is also well-known that the film of tear can breakup if the time between blinks is overly large or the layer of tear is very thin because of the tear glands in the eyes not producing enough tears. This phenomenon of the tear layer breaking up may be used to measure the dryness of the eye of a subject by measuring the time taken by the layer of tear on the surface of the eyeball of the subject to break up The subject is asked to blink once and asked not to blink again till asked to. The time between the blink and the appearance of the first tear breakup is measured and acts as a good measure of the lubrication of the eye. This is known as the non-invasive tear breakup time (TBUT or simply tear breakup time). Higher the TBUT, better is the eye lubricated.

To measure TBUT, a pattern having concentric light and dark areas, from a suitable light source, is projected on to the eyeball of the subject under assessment and the surface is observed, using a camera. The pattern helps in easily observing when the tear breakup occurs.

Such a light source produces multiple bright rings with intervening darker areas, which get reflected from the corneal surface. An imaging system used to image these rings reflected from the corneal surface. These rings retain their shape after specular reflection over smooth corneal surface. But one or more rings get deformed or broken in case the break-up falls on one or more bright rings reflected by the corneal surface. Therefore, detection of the first appearance of any deformation in the ring structure reflected from the surface of the subject's eye, after a blink, provides TBUT.

Different instruments are used to make these different measurements. The light sources used in each of them is different. Further the light sources use multiple light emitting device and hence the light sources are heavy. Further, such light sources may be heavy, bulky, are also not energy efficient, and produce waste heat.

SUMMARY OF THE DISCLOSURE

Thus, there has been a need for a light source which is light in weight and is energy efficient. Further, there has been a need for such a light source which meets the requirements of one or more of the instruments used for assessing dryness of a subject's eyes.

The present disclosure discloses a light source which may solve or mitigate one or more of the above said problems.

A substantially planar toroidal light source is disclosed. It is characterized by a substantially planar toroidal colorless translucent disc having a substantially concentric circular hole of a predetermined diameter, a substantially planar spiral coil of side emitting optical fiber, the coil having a predetermined pitch, the coil being attached to a first surface of the disc such that the coil and the disc are substantially concentric, wherein a first end of the coil is supplied with visible light from a light from a substantially point source of light for creating a toroidal disc of substantially uniform brightness at the second surface of the disc.

A light source for a device for measuring a height of a tear meniscus in an eye of a human subject, the light source comprising a substantially planar toroidal translucent colorless disc having a substantially concentric circular hole of a predetermined diameter, a substantially planar spiral coil of side emitting optical fiber, the coil having a predetermined pitch, the coil being attached to a first surface of the disc such that the coil and the disc are substantially concentric, wherein a first end of the coil is supplied with visible light from a substantially point source of light for creating a toroidal disc of substantially uniform brightness at the second surface of the disc, and the light from the second surface of the disc being obstructed by an opaque circle, for forming a circular image on a cornea of the eye of the human subject illuminated by the light source.

A light source for a device for measuring a tear breakup time in an eye of a subject, the light source comprising a substantially planar toroidal translucent colorless disc having a substantially concentric circular hole of a predetermined diameter, a substantially planar spiral coil of side emitting optical fiber, the coil having a predetermined uniform pitch, the coil being attached to a first surface of the disc such that the coil and the disc are substantially concentric, wherein a first end of the coil is supplied with visible light from a substantially point source of light for creating a toroidal disc of substantially uniform brightness at the second surface of the disc, and the light from the second surface of the disc being obstructed by an opaque cover with a plurality of substantially circular concentric transparent slits for casting the image of the slits on a cornea of the eye of the human subject illuminated by the light source.

A substantially planar toroidal light source characterized by a substantially planar toroidal translucent colorless disc having a substantially concentric circular hole of a predetermined diameter, a substantially planar spiral coil of side emitting optical fiber, the coil having a predetermined uniform pitch, the coil being attached to a first surface of the disc such that the coil and the disc are substantially concentric, and wherein the disc and the spiral coil are illuminated from a first side proximal to the coil, with a substantially point source of light positioned coaxially at a predetermined distance from the coil for the coil acting as a coiled cylindrical lens forming a planar spiral coil pattern brighter than a remaining part of the disc on a second side of the disc.

To further clarify advantages and features of the present invention, a more particular description of the invention will be rendered by reference to specific embodiments thereof, which is illustrated in the appended figures. It is to be appreciated that these figures depict only typical embodiments of the invention and are therefore not to be considered limiting of its scope. The invention will be described and explained with additional specificity and detail with the accompanying figures.

BRIEF DESCRIPTION OF THE FIGURES

The invention will be described and explained with additional specificity and detail with the accompanying figures in which.

Further, skilled artisans will appreciate that elements in the figures are illustrated for simplicity and may not have necessarily been drawn to scale. Furthermore, in terms of the construction of the device, one or more components of the device may have been represented in the figures by conventional symbols, and the figures may show only those specific details that are pertinent to understanding the embodiments of the present invention so as not to obscure the figures with details that will be readily apparent to those of ordinary skill in the art having benefit of the description herein.

DETAILED DESCRIPTION OF THE DISCLOSURE

For the purpose of promoting an understanding of the principles of the invention, reference will now be made to the embodiment illustrated in the figures and specific language will be used to describe the same. It will nevertheless be understood that no limitation of the scope of the invention is thereby intended, such alterations and further modifications in the illustrated system, and such further applications of the principles of the invention as illustrated therein being contemplated as would normally occur to one skilled in the art to which the invention relates.

It will be understood by those skilled in the art that the foregoing general description and the following detailed description are exemplary and explanatory of the invention and are not intended to be restrictive thereof.

The terms "comprises", "comprising", or any other variations thereof, are intended to cover a non-exclusive inclusion, such that a process or method that comprises a list of steps does not include only those steps but may include other steps not expressly listed or inherent to such process or method. Similarly, one or more devices or sub-systems or elements or structures or components proceeded by "comprises . . . a" does not, without more constraints, preclude the existence of other devices or other sub-systems or other elements or other structures or other components or additional devices or additional sub-systems or additional elements or additional structures or additional components. Appearances of the phrase "in an embodiment", "in another embodiment", and similar language throughout this specification may, but do not necessarily, all refer to the same embodiment.

Unless otherwise defined, all technical and scientific terms used herein have the same meaning as commonly understood by one of ordinary skill in the art to which this invention belongs. The system, methods, and examples provided herein are illustrative only and not intended to be limiting.

Embodiments of the present invention will be described below in detail with reference to the accompanying figures.

Figure 1:
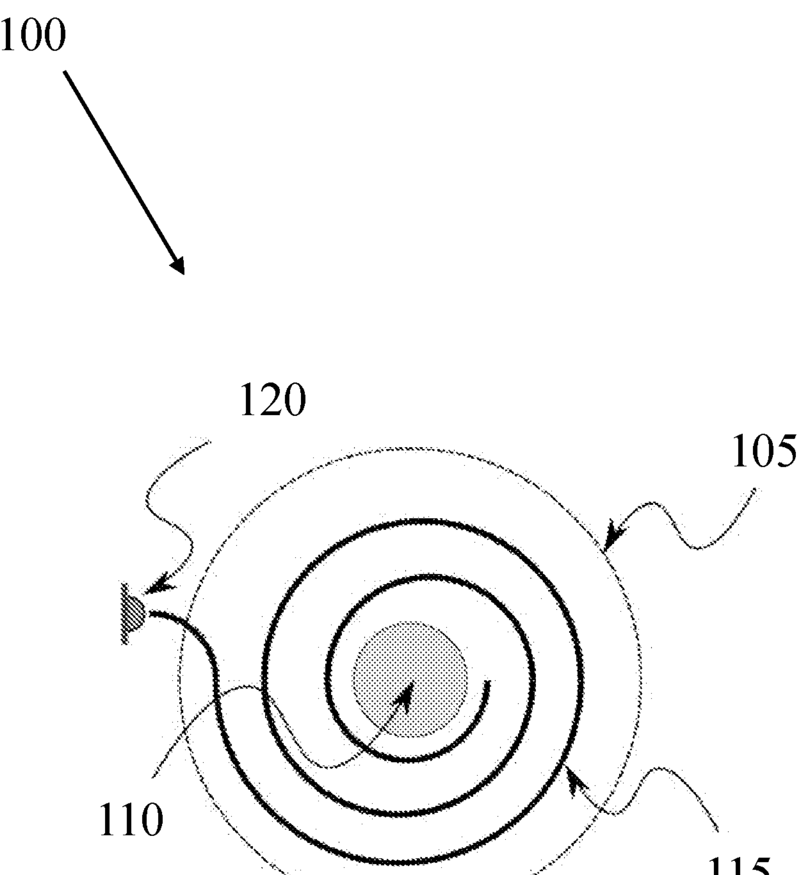
FIG. 1 shows an embodiment of the toroidal light source.

FIG. 1 shows a translucent circular disc 105. The disc 105 has a central substantially concentric circular hole 110 of a predetermined diameter. Herein, the term substantially is used to indicate that the hole is concentric excepting for manufacturing tolerances and acceptable errors. For the sake of brevity and clarity, the term "substantially" may be omitted in the description hereinafter, but it is intended and meant wherever applicable. On one surface of the disc 105, a first surface of the disc, is affixed a coil 115. The coil is made of an optic fiber. Hereinafter the coil and the optic fiber may be used interchangeably. The optic fiber is a side emitting optic fiber. As is known, while an optic fiber can work on total internal reflection and the light entering it at one end exits the other end substantially without attenuation over large distances. However, the side emitting optic fiber, though working on a similar principle, allows a certain amount of light to leak out of the sides and hence called side emitting optic fiber.

One end of the optic fiber 115, preferably the end closer to the outer circumference of the disc, is coupled to a substantially point source of light, preferably a source of white light, advantageously a light emitting diode 120 (hereinafter referred to as LED) emitting white light. Advantageously the LED 120 may be an LED known as a high intensity LED. The disc 105 being translucent, the light emitted by the sides of the optic fiber, impinges on the disc and is randomly scattered. Thus, the side of the disc 105 other than the side on which the coils 115 is disposed, the second side of the disc, appears substantially uniform. Thus, the disclosed arrangement, when the pitch of the coil is selected suitably, will create a toroidal light source of substantially uniform brightness.

Such a light source has the advantage of being low in weight because of the use of an LED. Further the thickness of such a light source may also be low which further, has the advantage that the whole device in which it is used may be made compact. This offers the further advantage that it is easier for the user to operate the device using the disclosed light source. Such a light source may be made out of frosted polycarbonate and may have the advantage that it is lighter than a light source using frosted glass, for example. Still further, the use of a high intensity LED provides the advantage that the disclosed light source is energy efficient.

Figure 2:
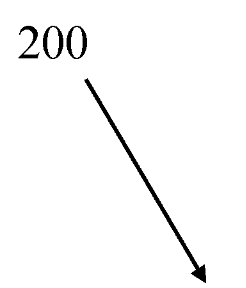
FIG. 2 shows an embodiment of the toroidal light source adopted for measuring the height of the tear meniscus.
Figure 2:
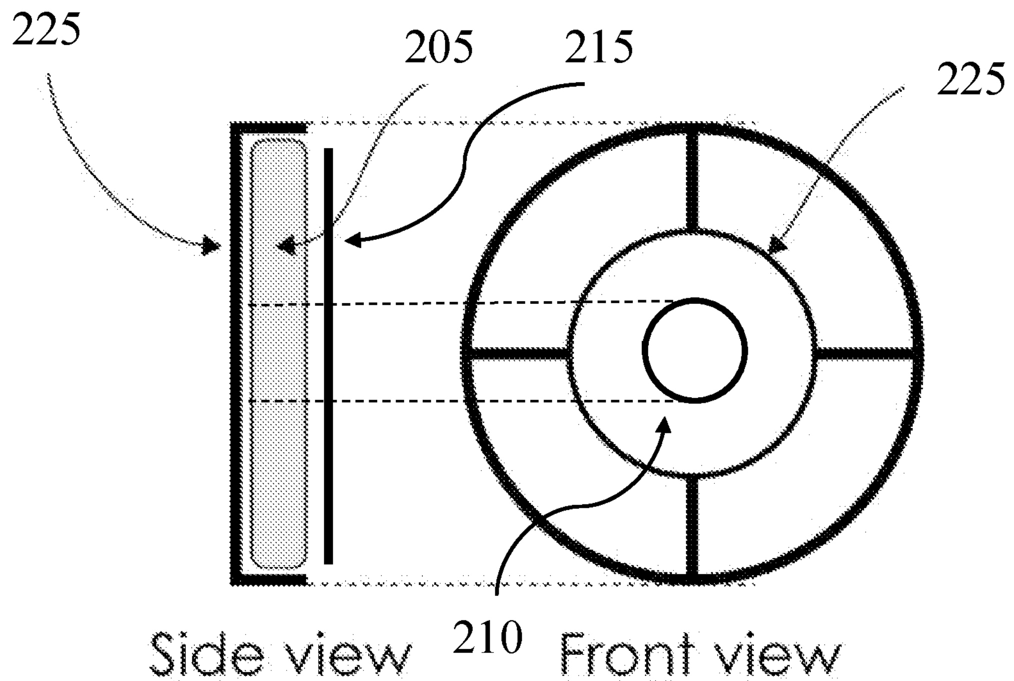

FIG. 2 shows the toroidal light source 200, which includes a translucent circular disc 205 and is similar to the light source 100 as described with reference to toroidal light source 100 of FIG. 1, fitted with a cover having a ring 225. The ring 225 has a predetermined radial width and is completely opaque to visible light. Thus, the coil 215, when coupled to the light from an LED (not shown) forms a toroidal light as described earlier with reference to FIG. 1. However, the light is obstructed by the ring 225 which casts an image of the ring on the cornea of the subject's eye as shown in FIG. 5.

Figure 5:
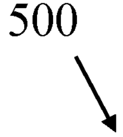
FIG. 5 shows the symbolic representation of the human eye with image of a ring projected in it.
Figure 5:
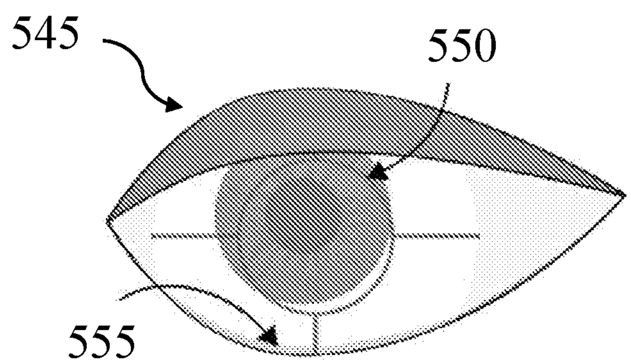

FIG. 5 shows the combination 500 of the human eye 545 and the image of the ring on the cornea of the human eye 545. FIG. 5 shows the human eye 545 symbolically. The image 550 of the ring 225 is shown on the cornea of the eye. The tear meniscus 555 is shown as a grey line over the dark line of the upper edge of the lower eyelid.

Figure 3:
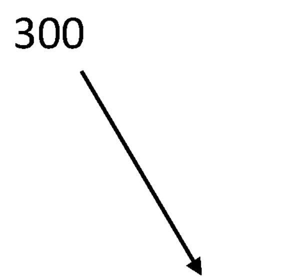
FIG. 3 shows an embodiment adopted for measuring the tear breakup time.
Figure 3:
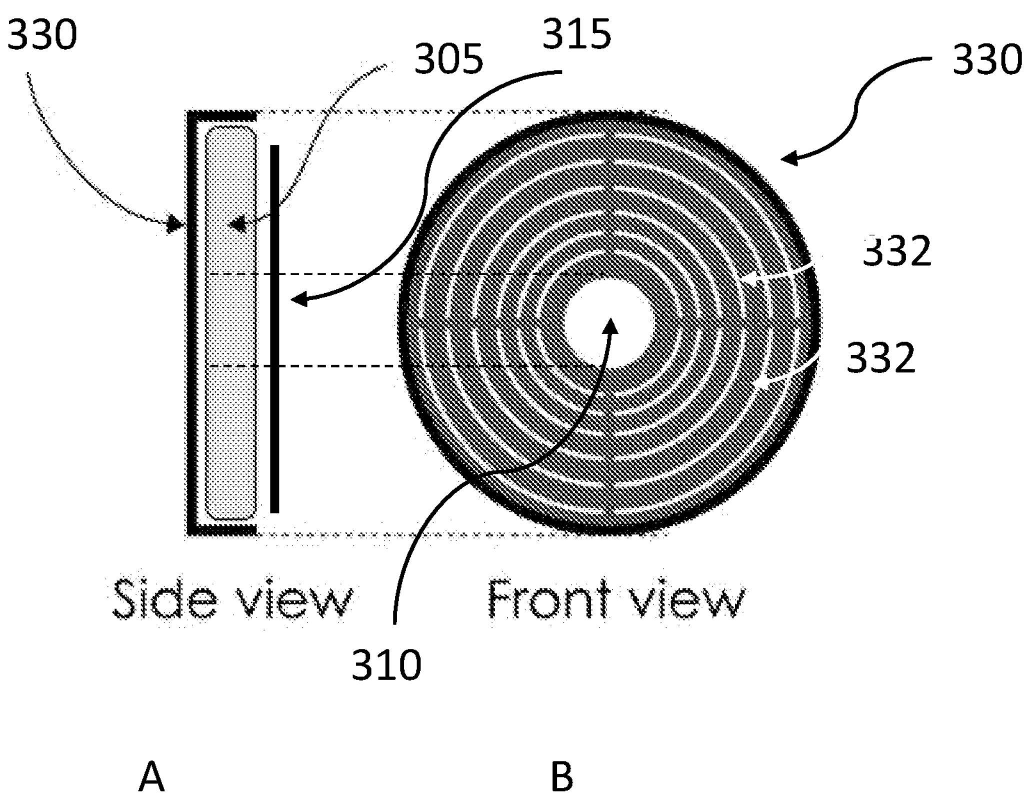

FIG. 3 shows the toroidal light source 300, which includes a translucent circular disc 305 and is similar to the light source 100 as described with reference to FIG. 1, fitted with an opaque cover 330 having a number of narrow concentric circular slits 332, two consecutive slits, both numbered 332 are shown with white arrows in FIG. 5. The slits 332 have a predetermined radial width. Thus, the coil 315, when coupled to the light from an LED (not shown) forms a toroidal light source 100 as described earlier with reference to FIG. 1. However, the light is obstructed by the ring cover 330 which has slits 332 creating concentric bright circular lines. Though the slits are referred to herein as circles, they are not complete circles because the opaque rings in between the slits are to be held to the cover 330 through very narrow tabs. However, for all practical purposes they are circles. This is shown in FIG. 7 wherein one of the bright lines 732 are indicated with a white arrow on the image of the human eye 745.

Figure 7:
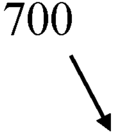
FIG. 7 shows the human eye on which a pattern of circular bright bands is projected.
Figure 7:
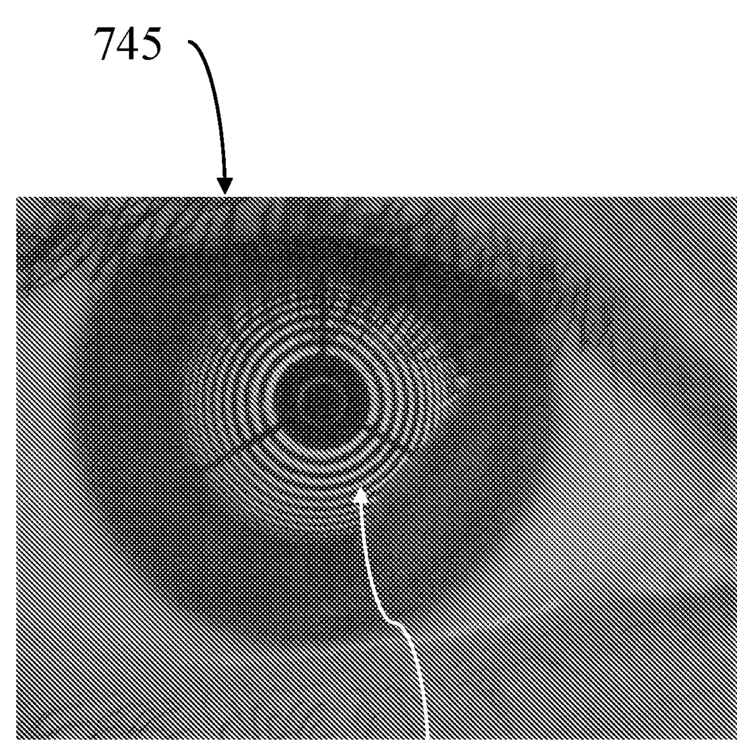

As can be seen from comparing FIG. 3 and FIG. 7, the circular opaque portions of the cover 330 is held in place by four spoke like projections whereas FIG. 7 shows only three. Suffice to say that such modifications, simplifications, improvements, and so on, to the features disclosed in this disclosure all fall within the scope of the matter disclosed in this disclosure. It is obvious to a person skilled in the art that a similar change, or even just two spokes are possible to be used with the cover 225 of FIG. 2 or cover 330 of FIG. 3. In a similar fashion, the pitch of the coil 115 of FIG. 1 and hence the bright lines 440 in FIG. 4 may also be different. All such variations fall within the purview of laboratory practice of a person of ordinary skill in the arts to which this disclosure belongs.

Figure 4:
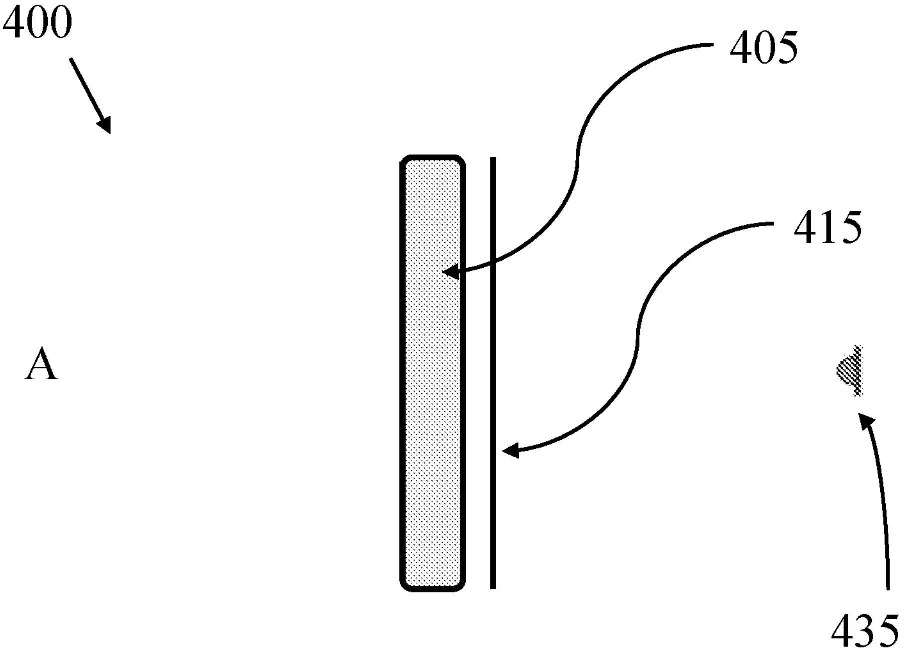
FIG. 4 shows another embodiment adopted for measuring the tear breakup time.
Figure 4:
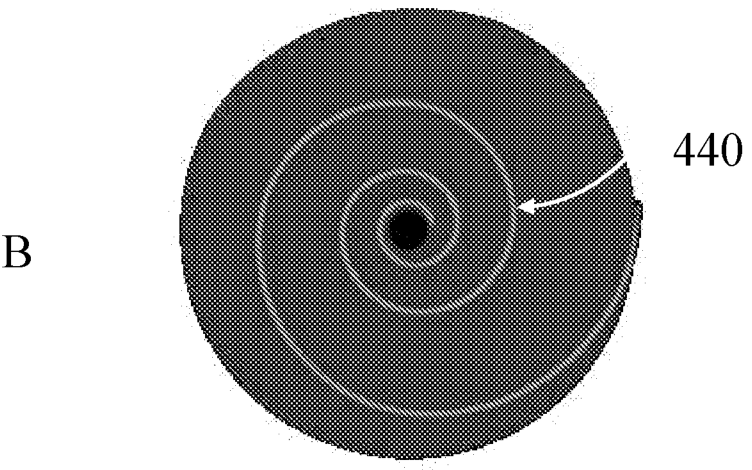

FIG. 4 shows an alternative method of creating a pattern of bright and dark that may be used in place of the bright circular rings formed using the embodiment described with reference to FIG. 3. Even though the pattern created by this embodiment is not of concentric circles, the narrow light and dark pattern serves the same purpose and enables the measurement of TBUT. This embodiment also has the disc 405 similar to the disc 105 described with reference to FIG. 1 and also the coil 415. However, instead of being couple to LED 120 as in the case of FIG. 1, the same coil 115 as described with reference to FIG. 1 is illuminated by LED 435 as shown in FIG. 4. The LED 435 is located on an imaginary line passing through the center of the circular disc 405, and is perpendicular to it. It is located at a predetermined distance from the disc 405 on the same side, the first side, of the disc 405 as the coil 415.

Figure 6:
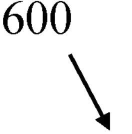
FIG. 6 shows the way the optic fiber acts as a cylindrical lens.
Figure 6:
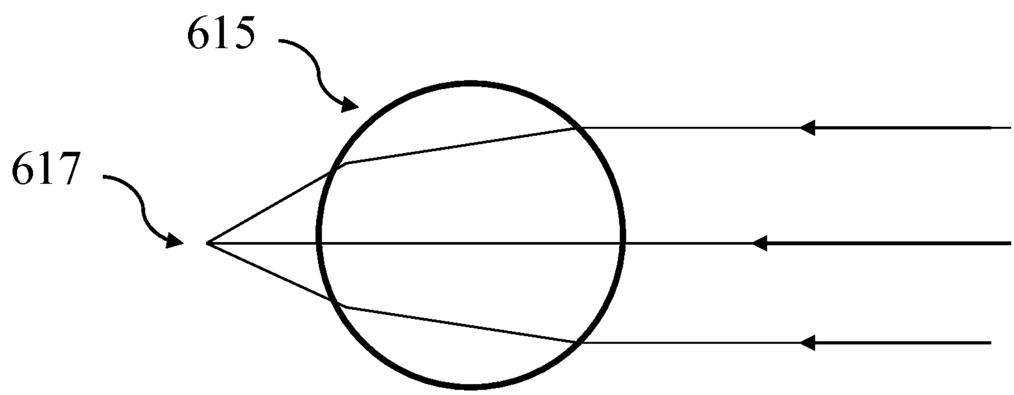

When the disc 405 and coil 415 are illuminated by light from LED 435, which is substantially a point source of light, the light impinging on the coil 415 is concentrated by the coil 415 acting as a cylindrical lens. This is indicated in FIG. 6 wherein one turn of the coil 615 is shown in cross-section and three rays of light from the LED are shown focused at one point 617. When this phenomenon is aggregated over the length of the fiber of the coil, the pattern shown as 440 in FIG. 4 results. This pattern, with a suitable pitch of the coil, may be used as a pattern in lieu of the pattern of light generated by the embodiment described with reference to FIG. 3.

While specific language has been used to describe the disclosure, any limitations arising on account of the same are not intended. As would be apparent to a person skilled in the art, various working modifications may be made to the method in order to implement the inventive concept as taught herein.

The figures and the foregoing description give examples of embodiments. Those skilled in the art will appreciate that one or more of the described elements may well be combined into a single functional element. Alternatively, certain elements may be split into multiple functional elements. Elements from one embodiment may be added to another embodiment. For example, orders of processes described herein may be changed and are not limited to the manner described herein. Moreover, the actions of any flow diagram need not be implemented in the order shown; nor do all of the acts necessarily need to be performed. Also, those acts that are not dependent on other acts may be performed in parallel with the other acts. The scope of embodiments is by no means limited by these specific examples. Numerous variations, whether explicitly given in the specification or not, such as differences in structure, dimension, and use of material, are possible. The scope of embodiments is at least as broad as given by the following claims.

We claim:

1. A planar toroidal light source, comprising:

a planar toroidal colorless translucent disc having a concentric circular hole of a diameter;

a planar spiral coil of side emitting optical fiber, the coil having a pitch, and the coil being attached to a first surface of the disc such that the coil and the disc are concentric, and wherein a first end of the coil is supplied with visible light from a point source of light for creating a toroidal disc of uniform brightness at a second surface of the disc.

2. The planar toroidal light source of claim 1, wherein the point source of light is an LED.

3. The planar toroidal light source of claim 2, wherein the LED is a white light emitting LED.

4. The planar toroidal light source of claim 1, wherein the pitch of the coil is equal to the diameter of the optical fiber.

5. The planar toroidal light source of claim 1, wherein the light from the point source of light is coupled to the optical fiber through a light coupler.

6. A light source for a device for measuring a height of a tear meniscus in an eye of a human subject, the light source comprising:

a planar toroidal translucent colorless disc having a concentric circular hole of a diameter;

a planar spiral coil of side emitting optical fiber, the coil having a pitch, and the coil being attached to a first surface of the disc such that the coil and the disc are concentric, wherein a first end of the coil is supplied with visible light from a point source of light for creating a toroidal disc of uniform brightness at a second surface of the disc, and the light from the second surface of the disc being obstructed by an opaque circle, for forming a circular image on a cornea of the eye of the human subject illuminated by the light source.

7. The light source of claim 6, wherein the opaque circle is formed on the disc employing a technique selected from a group of techniques comprising, painting, screen printing, etching, powder coating, and laser printing.

8. The light source of claim 6, wherein the opaque circle is detachably attached to the disc.

9. A light source for a device for measuring a tear breakup time in an eye of a human subject, the light source comprising:

a planar toroidal translucent colorless disc having a concentric circular hole of a diameter:

a planar spiral coil of side emitting optical fiber, the coil having a uniform pitch, and the coil being attached to a first surface of the disc such that the coil and the disc are concentric, wherein a first end of the coil is supplied with visible light from a point source of light for creating a toroidal disc of uniform brightness at a second surface of the disc, and the light from the second surface of the disc being obstructed by an opaque cover with a plurality of circular concentric transparent slits for casting the image of the slits on a cornea of the eye of the human subject illuminated by the light source.

10. The light source of claim 9, wherein the opaque cover with the plurality of circular concentric transparent slits are formed on the disc employing a technique selected from a group of techniques comprising painting, screen printing, etching, powder coating, and laser printing.

11. The light source of claim 9, wherein the opaque cover with the plurality of circular concentric transparent slits is detachably attached to the disc.

12. A planar toroidal light source, comprising:

a planar toroidal translucent colorless disc having a concentric circular hole of a diameter;

a planar spiral coil of side emitting optical fiber, the coil having a uniform pitch, and the coil being attached to a first surface of the disc such that the coil and the disc are concentric, and wherein the disc and the coil are illuminated from a first side proximal to the coil, with a point source of light positioned coaxially at a distance from the coil for the coil acting as a coiled cylindrical lens forming a planar spiral coil pattern brighter than a remaining part of the disc on a second side of the disc.

* * * * *